United States Patent [19]

Field

[11] 4,054,740

[45] Oct. 18, 1977

[54] HYDROXYBIOTIN

[75] Inventor: George Francis Field, West Caldwell, N.J.

[73] Assignee: Hoffmann-La Roche Inc., Nutley, N.J.

[21] Appl. No.: 610,707

[22] Filed: Sept. 5, 1975

Related U.S. Application Data

[63] Continuation-in-part of Ser. No. 536,139, Dec. 24, 1974, abandoned.

[51] Int. Cl.$^2$ .................................................. C07D 495/04
[52] U.S. Cl. ........................... 548/303; 260/332.2 A; 260/455 B; 260/534 E; 260/561 N; 560/12; 560/13; 560/16; 560/153; 560/156
[58] Field of Search ........................................ 260/309.7

[56] References Cited

U.S. PATENT DOCUMENTS

| 2,436,851 | 3/1948 | Businger | 260/309.7 X |
| 2,489,234 | 11/1949 | Goldberg et al. | 260/309.7 |
| 2,489,236 | 11/1949 | Goldberg et al. | 260/309.8 |
| 3,740,416 | 6/1973 | Gerecke et al. | 260/309.7 |

OTHER PUBLICATIONS

Safir et al., J. Org. Chem., 1947, vol. 12, pp. 475–482.

*Primary Examiner*—Natalie Trousof
*Attorney, Agent, or Firm*—Samuel L. Welt; Bernard S. Leon; Richard A. Gaither

[57] ABSTRACT

This invention relates to a synthesis of biotin by the reduction of dehydrobiotin. The dehydrobiotin is prepared from 6-hydroxy-7-nitro-heptanoic acid methyl ester. Novel intermediates are also obtained by this synthesis.

3 Claims, No Drawings

HYDROXYBIOTIN

CROSS REFERENCE TO RELATED APPLICATIONS

This application is a continuation-in-part application of Ser. No. 536,139, filed Dec. 24, 1974, now abandoned.

BACKGROUND OF THE INVENTION

This invention relates to a process of preparing biotin by the reduction of dehydrobiotin. Biotin, vitamin H, is a natural product found largely in the kidney, liver, egg yolk, milk and yeast. The compound is used to prevent symptoms of egg-white injury in experimental animals. Its prime medical use is in various dematitides.

Biotin has been prepared synthetically by Harris et al. (Science, 97, 447 (1943) and Baker et al. (J. Org. Chem., 12, 167 (1947), among others. None of these syntheses, however, were commercially feasible. The first commercial synthesis of biotin resulted from the work of Goldberg and Sternbach (U.S. Pat. Nos. 2,489, 2,489,235 and 2,489,236).

Safir et al., in an article entitled "A Synthesis of d,1-Dehydrobiotin" (J. Org. Chem. 12, 475 (1947), disclose the preparation of a compound believed to be 2-(δ-carboxybutyl)-3-amino-4-ketothiophane starting from 7-carbethoxy-2-heptenoic acid. The ketothiophane is subsequently treated with potassium cyanate to yield a product having a melting point of 175°–176° C. The authors assumed this product to be dehydrobiotin. The subsequent reduction of this product to biotin is not illustrated in the article.

It has now been discovered that the Safir et al. process does not result in the formation of 2-(δ-carboxybutyl)-3-amino-4-ketothiophane. Furthermore, the compound treated with potassium cyanate (according to Safir et al.) results in a product other than dehydrobiotin, as will be pointed out hereinafter.

SUMMARY OF THE INVENTION

This invention is directed to a process for synthesizing d,1, or d,1-biotin or derivatives which have the formula:

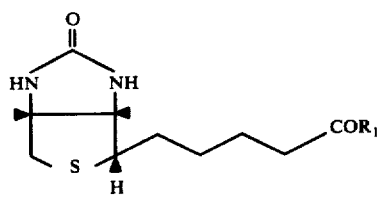

from the reduction of dehydrobiotin or derivatives thereof having the formula:

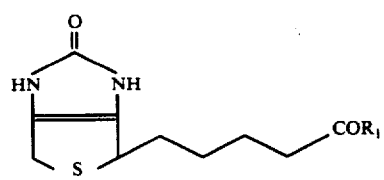

wherein $R_1$ is lower alkoxy, hydroxy or an unsubstituted or substituted amino group, which, in turn, is prepared from a compound of the formula:

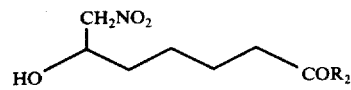

wherein $R_2$ is lower alkoxy, or an unsubstituted or substituted amino group.

By means of this process, biotin can be economically produced in high yields.

DETAILED DESCRIPTION OF THE INVENTION

The term "lower alkyl" as used herein, refers to an alkyl group having saturated aliphatic straight or branched chains of 1–6 carbon atoms. Exemplary of the alkyl groups contemplated are methyl, ethyl, propyl, isopropyl, butyl and the like.

The term "lower alkyl amine" as used herein, refers to amine compounds wherein the alkyl moiety is as previously defined. Exemplary of the contemplated compounds are methylamine, ethylamine, diethylamine, triethylamine, isopropylamine, hexylamine and the like.

The term "lower alkyl acid halide" as used herein, refers to organic acid halides wherein the alkyl moiety is as previously defined. Exemplary of the compounds contemplated are acetyl chloride, acetyl bromide, propionyl bromide, butyryl chloride, isobutyryl bromide, valeryl chloride and the like.

The term "halogen" as used herein, refers to chlorine, bromine, iodine, and fluorine unless otherwise specified.

The term "aryl" (designated Ar) as used throughout the application includes mono-nuclear aryl groups such as phenyl which can be unsubstituted or substituted in one or more positions with a lower alkyl, halogen, lower alkoxy, amino, nitro, mono- and di-lower alkylamino.

The term "alkali metal" as used herein, refers to sodium, potassium, lithium, cesium, rubidium, unless otherwise specified.

The term "lower alkoxy" as used herein, refers to lower alkoxy wherein the alkyl moiety is as previously defined. Exemplary of the groups contemplated are those such as methoxy, ethoxy, propoxy and the like.

The term "alkaline earth metal" refers to calcium, zinc, magnesium, barium, unless otherwise specified.

As still further used throughout this application, in the pictorial representations of the compounds of this application, a thickened tapered line (▲) indicates a substituent which is in the β-orientation (above the plane of the molecule), a dotted line (----) indicates a substituent which is in the α-orientation (below the plane of the molecule) and a wavy line (∼) indicates a substituent which is in either the α- or β-orientation. It is to be understood that the pictorial representations of the compounds given throughout the specification are set forth for convenience and are to be construed as inclusive of other forms, including enantiomers and racemates, and are not to be construed as limited to the particular form shown.

In accordance with this invention, d,1, or d,1-biotin and derivatives thereof are obtained by the reduction of d,1-dehydrobiotin or derivatives thereof. Dehydrobiotin, d,1-2,3,4-tetrahydro-2-oxo-1H-thieno-[3,4-d]- imidazole-4-pentanoic acid, is prepared according to a novel process, more fully set out hereinafter, wherein a compound of formula III is the starting material. The compound of formula III may be obtained either (a) by treating 5-carbomethoxyvaleraldehyde with nitromethane and base (according to the procedure of Grob, *Helvetica Chemica Acta.*, 35, 885 (1952)) or (b) by treating 5-carbomethoxyvalerylchloride with hydrogen in the presence of palladium on carbon and sodium acetate. The resulting product is then treated with nitromethane in the presence of base.

The preparation of compound III may be illustrated as follows:

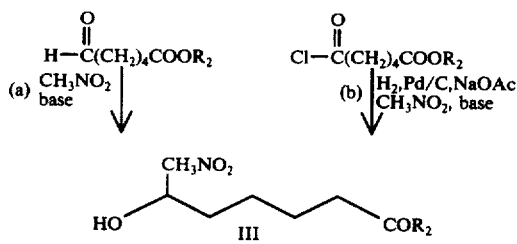

wherein $R_2$ is as previously defined.

In carrying out either of the above reactions, the ratio of the nitromethane to compound IV is from about 1:1 to about 10:1, preferably from about 1:1 to about 2:1, on a molar basis. These reactions may be carried out in any inert solvent. Typical inert solvents are those such as diethyl ether, benzene, toluene, ethanol and the like. Temperature and pressure are not critical in carrying out these reactions. Temperatures of about 0° to about 75° C. and atmospheric pressure are quite suitable. The temperature is preferably about 25° C. The base may be any of the conventional bases such as sodium hydroxide, sodium hydride, sodium methoxide, potassium hydroxide, ammonia and the like. As well as primary, secondary, and tertiary lower alkyl amines. The amount of base used may be from about 0.1:1 to about 1:1, on a molar basis, per mole of compound IV.

Compound III is converted to compound IV which has the formula:

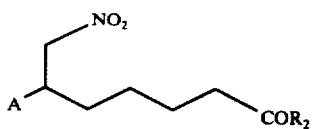

wherein A is halogen, ArSO$_2$,

and similar type leaving groups; $R_2$ is as previously defined, and $R_3$ is lower alkyl or aryl; by reacting compound III with reagents selected from $PX_3$, $PX_5$, $SO_2X$, $COCl_2$, $ZnCl_2$, HX, $CH_3C_6H_4SO_2$; $R_3COX$ (wherein X is halogen) and $R_3$ is as previously defined.

Compound IV is subsequently reacted with mercaptoacetic acid ($HSCH_2CO_2H$) in the presence of a base to form, after acidification, a compound of the formula:

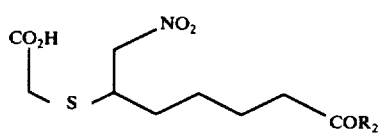

wherein $R_2$ is as previously defined.

Compound V may be converted to a compound having the formula:

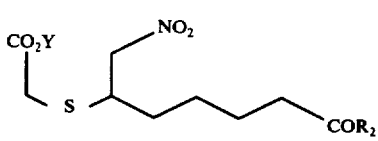

wherein Y is an alkali metal or alkaline earth metal cation, or a substituted or unsubstituted ammonium group and $R_2$ is as previously defined.

A particularly convenient salt for characterization purposes is the dicyclohexylamine salt of compound VI which has the formula:

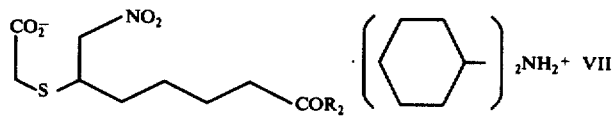

wherein $R_2$ is as previously defined.

Compound VII may alternatively be prepared by using as a starting material a compound having the formula:

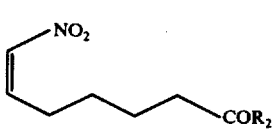

wherein $R_2$ is as previously defined.

Compound IVa is obtained by the treatment of compound IV with a base. The base employed may be any of those mentioned hereinbefore. Compound IVa is treated with mercaptoacetic acid to form compound V. Compound VII is then prepared according to the procedures described hereinbefore.

Compounds V, and VI, as well as the processes for their preparation are novel and form another aspect of this invention. The reaction sequence from compounds III to VI may also be suitably carried out in one reaction vessel without isolation of intermediates. The reaction proceeds as illustrated below:

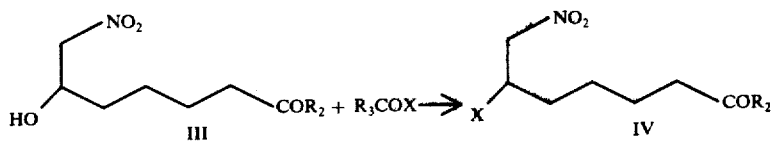

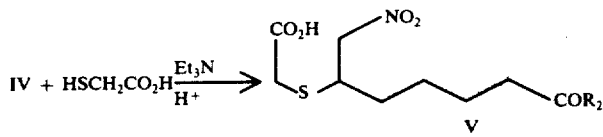

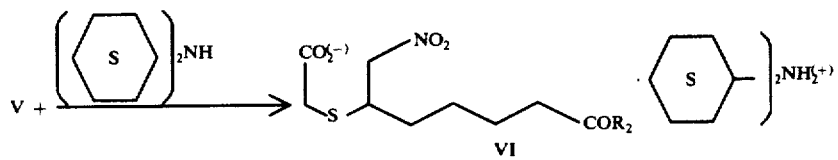

In carrying out the above sequence, the ratio of acid halide to compound III is from about 1:1 to about 5:1 on a molar basis, preferably about 1:1 to about 1.5:1. The amount of mercaptoacetic acid employed is from about 1:1 to about 10:1, preferably about 1:1 to 1.5:1, on a molar basis, based on compound III. The ratio of lower alkylamine employed, based on compound III, is from about 2:1 to about 10:1, preferably about 2:1 to about 3:1 on a molar basis. The proportion of dicyclohexylamine employed based on compound III, is from about 1:1 to about 10:1, preferably from about 1:1 to about 2:1, on a molar basis. Although the above reaction scheme employs an acid halide to form compound IV, it is to be understood that any of the other above-mentioned reagents are employed in a similar fashion. The ratio of any of these reagents to compound III is from about 1:1 to about 5:1, preferably about 1:1 to about 1.5:1, on a molar basis.

Although triethylamine is illustrated as the base utilized, it is to be understood that any of the previously mentioned bases may be also used.

In carrying out the above sequence, conventional solvents, such as those previously mentioned, may be employed. The pressure and temperature utilized are not critical. Generally, atmospheric pressure and temperatures of about 0° C. to about 50° C. are quite suitable.

Compounds V and VI contain an asymmetric center and may be resolved by conventional techniques with conventional resolving agents.

The reaction of compound V with dicyclohexylamine is merely to render it storage stable and is not necessary if the process is being conducted continuously.

Compound V or the dicyclohexylamine salt thereof (compound VI) is converted to a compound of the formula

VIII

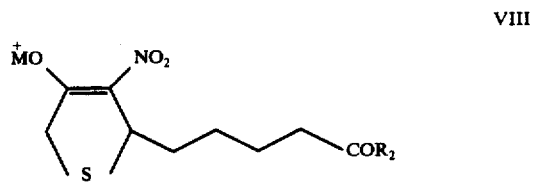

wherein $R_2$ is as previously defined and M is a cation derived from an alkali or alkaline earth metal, M may also be a substituted or unsubstituted ammonium, or a proton.

The conversion of compound V to compound VIII is accomplished by activation of the carboxyl group of the mercaptoacetic moiety of compound V and treatment with a base. A particularly useful method of activation said carboxyl group is by the formation of its phenyl esters. These phenyl esters are prepared by treatment of compound V with a dehydrating agent, e.g., N,N-dicyclohexylcarbodiimide, and a substituted or unsubstituted phenol. Compound VI may also be employed to form compound VIII. When this latter alternative is utilized, compound VI is first acidified to compound V before proceeding to compound VIII.

The reaction proceeds according to the following sequence:

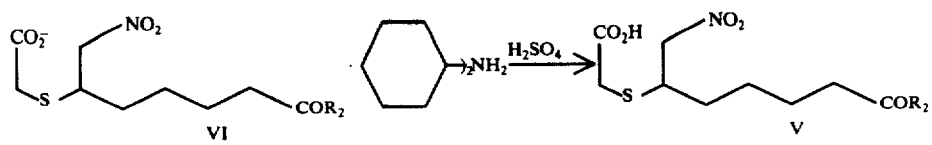

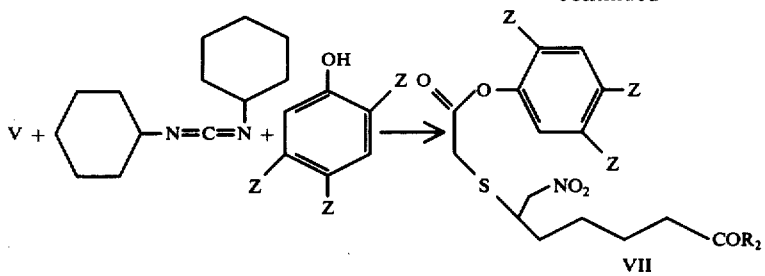

wherein $R_2$ and Y are as previously defined and Z is hydrogen, halogen, nitro, —CN, lower alkoxy and lower alkylsulfonyl.

The ring closure is effected by treatment with a base, particularly a lower alkylamine or an alkali, alkaline earth metal or ammonium salt of a lower alkyl carboxylic acid, preferably sodium acetate, as illustrated below:

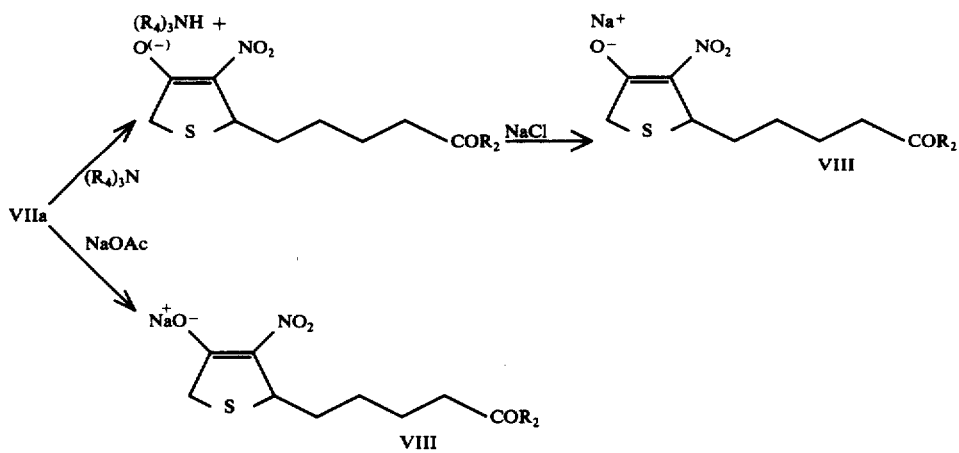

wherein $R_4$ is lower alkyl and $R_2$ is as previously defined.

It should be appreciated that compound VIII can exist in the keto from VIIIa, which is still another aspect of this invention. Salts of the enol form of compound VIII are convenient for ease for characterization and storage. Compound VIIIa has the formula:

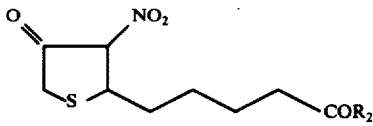

wherein $R_2$ is as previously defined.

Compounds VII, VIII, and VIIIa are novel and form yet another aspect of the instant invention. Compounds VIII and VIIIa contain an asymmetric center and may be resolved by conventional techniques using conventional resolving agents.

In carrying out the above reaction sequence, dilute sulfuric acid (25% V/V) is used to form the free acid (compound V) from compound VI. The amount of sulfuric acid used is not critical and is readily determinable by one skilled in the art practicing this invention. The amount of 2,4,5-trichlorophenol employed may be from 1:1 to about 10:1, preferably about 1:1 to 2:1, on a molar basis, per mole of compound V. The proportion of N,N-dicyclohexylcarbodiimide and lower alkylamine (when that procedure is utilized) will vary from about 1:1 to about 10:1, preferably from about 1:1 to about 2:1, on a molar basis, per mole of compound V.

The dehydrating agents utilized are not critical and may be those generally known, such as thionyl chloride, lower alkylchloroformate, and other known carbodiimide compounds.

The phenolic moiety need not be limited to the trichlorophenol illustrated. Typical substitute phenols that may be employed are mono, di, and trihalo substituted phenols, mono, di, and trinitro substituted phenols and the like as illustrated hereinabove.

When the sodium acetate procedure is utilized, the above conditions are generally applicable. The proportion of sodium acetate used will vary from about 2:1 to about 10:1, preferably about 2:1 to about 10:1, preferably about 2:1 to about 4:1, on a molar basis, per mole of compound V.

Either procedure is carried out in the presence of inert solvnents.

In carrying out the above sequence, whether according to the lower alkylamine or sodium acetate procedure, temperature and pressure are not critical. Atmospheric pressure and temperatures of from about 0°. to about 25° C., preferably from about 5°C. to about 15° C., are quite suitable.

Other methods of activation of the carboxyl group of compound V may be used in the formation of compound VIII, for example, treatment of compound V with an anhydride, such as acetic anhydride in the presence of a base, particularly sodium acetate or a lower alkyl tertiary amine. The reaction sequence is as follows:

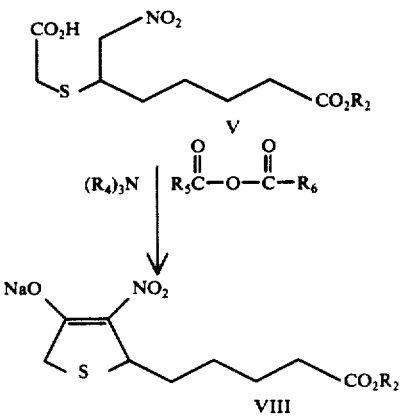

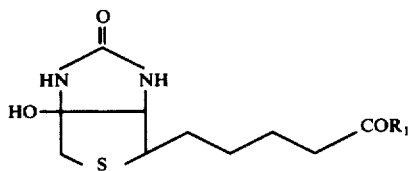

wherein $R_1$ and $R_4$ are as previously defined, $R_5$ and $R_6$ are lower alkyl group which may be the same or different.

Although the acetic anhydride has been illustrated, any lower alkyl anhydride may be employed. The ratio of lower alkyl anhydride employed may be from about 2:1 to 10:1, preferably from about 2:1 to about 5:1, based on compound V. In addition to lower alkylamine bases, sodium acetate may also be utilized. The ratios of either lower alkylamine or sodium acetate in this procedure is as previously stated.

Compound VIII is converted to a compound of the formula:

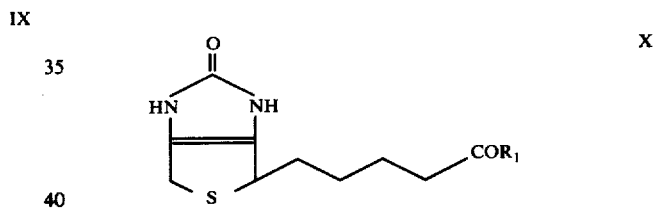

wherein $R_1$ is as previously defined.

Compound IX is novel and forms yet another aspect of the invention. This compound has three centers of asymmetry and may be resolved into its optical antipodes by conventional methods utilizing conventional resolving agents.

A typical reaction sequence from compound VIII to compound IX, is as follows:

pentanoic acid (hydroxybiotin) compound VIII is reduced under acid conditions to form the acid addition salt, compound VIIIb. VIIIb is subsequently reacted with an alkali metal cyanate to form compound IX.

The reduction step may generally be carried out by hydrogenating at a temperature of about 25°. to about 75° C., preferably about 25°-50° C. The hydrogen pressure will generally range from about 10 psig to about 1000 psig, preferably about 500 psig. Conventional supported and unsupported hydrogenation catalysts may be utilized. Typical hydrogenation catalysts are platinum (finely divided), palladium (finely divided), Raney nickel and copper-chromium oxide. An alternative method of preparing compound VIIIa is to treat compound VIII with chemical reducing agents such as zinc metal, iron, or stannous chloride in the presence of a strong acid.

The particular acids used in either procedure are not critical and may be selected from acids such as hydrochloric, nitric, sulfuric, phosphoric, trichloroacetic, hydrobromic, hydroiodic, chloroacetic and trifluoroacetic. These acids may be used alone or in combination.

The reaction of Compound VIIIa, with alkali metal cyanate to form compound X occurs under temperature and pressure conditions ranging from about 0°. to about 75° C., preferably 25°. to 50° C. and atmospheric pressure. The amount of alkali metal cyanate employed will vary from about 2:1 to about 10:1, preferably from about 2:1 to about 4:1, on a molar basis, per mole of compound VIIIa.

Compound IX is then converted by dehydration to a compound of the formula:

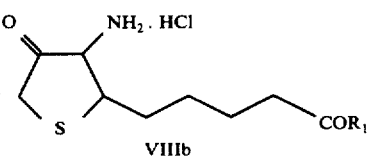

wherein $R_1$ is as previously defined.

Compound X is novel and forms still another aspect of the instant invention. Compound X contains an asymmetric carbon atom and may be resolved by conventional techniques using conventional resolving agents.

The dehydration of compound IX to compound X is conducted under acid conditions. The particular acid or

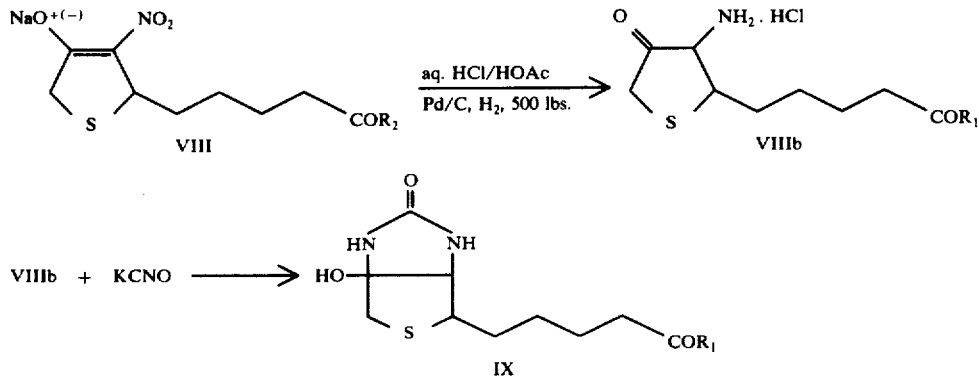

wherein $R_1$ and $R_2$ are as previously defined.

In carrying out the above sequence to form hexahydro-6a-hydroxy-2-oxy-1H-thieno[3,4-d]imidazole-4- amounts thereof used are not critical. As a matter of fact, the previously mentioned acids may be used to effect the formation of compound IX. If desired, typical dehydration agents such as $P_2O_5$, $SOCl_2$, $H_2SO_4$, $H_3PO_4$, $ZnCl_2$, acetic anhydride and activated alumina may also be employed in conjunction with the acid. Likewise, the pressure and temperature conditions are not critical and may vary from about 0°C. to about 75° C., preferably 25°C. to about 50° C., and atmospheric pressure.

Compound X is then converted to a compound of the formula:

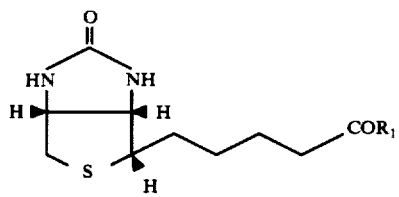

wherein $R_1$ is as previously defined.

The formation of compound I is accompanied by reduction with a conventional reducing agent. Among the preferred reducing agents that may be employed are complex metal hydrides such as sodium borohydride or the boranetrimethylamine complex alone or in admixture with a lower alkyl carboxylic acid, such as acetic acid, or a mineral acid. Mixtures of a Lewis acid and a lower alkylsilane such as, triethylsilane and trifluoroacetic acid are also reducing agents within the scope of this invention. Temperatures and pressures are not critical and will generally be from about 25°. to about 1502 C., preferably 25°. to 50° C. and atmospheric pressure.

The enantiomeric form of biotin obtained, i.e., d-,l-, or a d,l-mixture will be governed by the antipode of compound X that is reduced.

In turn, the esters or amides obtained by the process may be hydrolyzed to biotin.

The following non-limiting examples illustrates the process of the invention and the novel intermediates obtained. All temperatures are in degrees Centigrade and pressures are psig. The ether used is diethyl ether.

EXAMPLE 1

The following example illustrates the preparation of 6-carboxymethylthio-7-nitroheptanoic acid, methyl ester dicyclohexylamine salt.

A mixture of 82 g. (0.4 moles) of 6-hydroxy-7-nitroheptenoic acid methyl ester and 35 ml. (38.5 g., 0.49 moles) of acetyl chloride in a 500 ml. flask is stirred without heat under a drying tube. The reaction mixture becomes cold until the solid dissolves. At this point, it becomes violently exothermic and large volumes of hydrogen chloride are given off. The reaction mixture is cooled in an ice bath to keep the reaction under control. When the reaction has subsided, it is stirred in an oil bath at 45°-50°for about 50 minutes until the evolution of gas subsides. Then 50 ml. of benzene is added and the mixture concentrated on the rotary evaporator to remove any unreacted acetyl chloride. The residue (ca. 100 g.) and 43.24 g. (0.46 moles) of 98% mercaptoacetic acid are dissolved in 1.5 liter of ether. This solution is stirred and cooled to 10°in an ice bath and 120 ml. (87 g., 0.86 moles) of triethylamine was added over a 10 minute period. The reaction is exothermic and warms up to room temperature. The cooling bath is removed and the mixture stirred at ambient temperature for 3.5 hours. Thin layer chromatography of an aliquot on a silica microplate run with 25% EtOAc/hexane and visualized with ammonia vapor and then iodine should show no spot of $R_f$0.5 (i.e., acetate or starting alcohol). The reaction mixture is diluted with 1 liter of water and 500 ml. of 3N hydrochloric acid. The organic phase is washed 4 times with 500 ml. of distilled water. To the organic phase is added 87.4 ml. (0.44 moles) of dicyclohexylamine. With cooling, a brown oil separates. This product crystallizes only slowly. The sides of the flask are seeded and scratched at the surface of the liquid. The oil at the bottom should be kept agitated to prevent the formation of a hard cake. After cooling overnight in the refrigerator, 172 g. (93% yield) of product, m.p. 95°-102°is collected and washed with ether. The product is identified as the dicyclohexylamine salt of 6-carboxymethylthio-7-nitroheptanoic acid, methyl ester.

EXAMPLE 2

Preparation of 5-(2,5-dihydro-4-hydroxy-3nitrothien-2-yl)pentanoic acid methyl ester, sodium salt The following example illustrates the preparation of the captioned compound by the triethyl amine procedure to hereinabove.

A mixture of 1 liter of ether, 500 ml. of water, 92.2 g. (0.2 mole) of 6-carboxymethylthio-7-nitroheptanoic acid, methyl ester, dicyclohexylamine salt and 100 ml. of dilute sulfuric acid (⅓, v/v) is shaken until the solid has dissolved. The organic phase is separated, washed with 250 ml. of water and 250 ml. of brine (saturated) and dried with sodium sulfate. To this solution of the free acid is added 43.44 g. (0.22 mole) of 2,4,5-trichlorophenol and this mixture is cooled in an ice bath to 5°. To this cold, stirred solution is added a solution of 46.4 g. (0.225 mole) of N,N-dicyclohexyl carbodiimide in 100 ml. of ether. The reaction mixture is stirred in the ice bath for 0.5 hour and then in a water bath at 25°for 1 hour. The precipitated dicyclohexyl urea is filtered off and washed with 100 ml. of dry ether. The ethereal filtrate is returned to the reaction flask and cooled to 5°. Then 40 ml. (0.29 mole) of triethylamine is added dropwise during 0.5 hour to the cold stirred solution. The reaction mixture is then stirred cold for ½ hour and stored overnight in the refrigerator. It is then stirred with 500 ml. if saturated salt solution and seeded and scratched to induce crystallization of the product. After about 15 minutes of stirring, the solid is collected, washed with about 200 ml. of ether and dried in the vacuum oven at room temperature over Drierite to give 40 g. of brown solid. Analysis by uv ($\lambda_{max}$ 345 $_{NMR}$ ($\epsilon$ 16,000 ) indicated a content of 64$ of 5-(2,5-dihydro-4-hydroxy-3-nitrothien-2-yl)pentanoic acid methyl ester, sodium salt (i.e., 25.7 g. or 45%). Recrystallization from methanol provided a pure product having a m.p. of 193°-198°(dec.).

EXAMPLE 3

The compound of Example 2 is alternatively prepared using the sodium acetate procedure in the following manner:

A mixture of 6-carboxymethylthio-7-nitroheptanoic acid, methyl ester, dicyclohexylamine salt (78 g., 0.169 mole), 750 ml. of ether, 650 ml. of water and 130 ml. of 25% (v/v) sulfuric acid is stirred until the solid had dissolved. The organic layer is separated, washed two times with 250 ml. of water and 250 ml. of brine and dried over sodium sulfate. The organic layer is subsequently concentrated on the rotary evaporator to leave ca. 48 g. of orange oil. This is dissolved in 500 ml. of ethyl acetate. To this solution is added 35.6 g. (0.18 mole) of 2,4,5-trichlorophenol (technical) and the solution is cooled to 5° in an ice bath and stirred. A solution of 37.3 g. (0.18 mole) of N,N-dicyclohexyl carbodiimide in 200 ml. of ethyl acetate is added to this stirred solution. This mixture is stirred in the ice bath for 0.5 hour and then in a water bath at 25° for 1 hour. The precipitated dicyclohexyl urea is filtered off and washed with 100 ml. of ethyl acetate. The filtrate is returned to a 1 liter three-necked round bottom flask with stirrer, thermometer and calcium chloride drying tube and re-cooled in an ice bath to ca. 5°. Then 29.5 g. (0.36 mole) of sodium acetate (anhydrous) is added. The reaction mixture is stirred to 0° for 1 hour and then the cooling bath is removed. The mixture is stirred overnight without cooling. The solid is collected, washed with 50 ml. of ethyl acetate and dried in the vacuum oven over Drierite at room temperature to give 63.29 g. of crude product. The ultraviolet spectrum of an aliquot indicated it to be 42% product (26.58 g., 56%).

EXAMPLE 4

A third alternative procedure for the preparation of the compound of Example 2 is illustrated below.

To a solution of 5.6 g. (20 mmole) of 6-carboxymethyl-thio-7-nitroheptanonic acid methyl ester and 4 (39 mmole) ml. of acetic anhydride in 50 ml. of anhydrous ether cooled to 0° was added 5 ml. (39 mmole) of triethylamine. This mixture was kept at 4° for 19 hr. Then 50 ml. of saturated sodium chloride was added to the stirred reaction mixture. The pH of the aqueous phase was adjusted to 7 with 10N sodium hydroxide and the solid was collected and washed with ethyl acetate to give 2.45 g. of crude product. Analysis by ultraviolet spectrum indicated a product content of 49% for a yield of 21%.

EXAMPLE 5

Preparation of hexahydro-6a-hydroxy-2-oxo-1H-thieno[3,4-d]-imidazole-4-pentanoic acid (hydroxybiotin)

A solution of 26 g. of the crude compound of Examples 2-4, equivalent to 12.75 g. (45 mmol), in 450 ml. of acetic acid was diluted with 90 ml. of 3N hydrochloric acid and hydrogenated over 5 g. of 10% Pd/C at 500 lb. pressure at room temperature overnight. Hydrogen absorption was very slow after about 3 hours. The yellow solution was filtered to remove the catalyst and concentrated in vacuo at 45° to leave ca. 40 g. of residue. This was diluted with 100 ml. of water and filtered to remove a small amount of solid which was washed with 50 ml. of water. The combined filtrates were washed with 150 ml. of ether. The aqueous phase was cooled in an ice bath and treated with a solution of 7.6 g. (93.7 mmol) of potassium cyanate in 20 ml. of water to give an orange solution with pH 3-4. After stirring for 1.2 hours without cooling, this solution was neutralized with solid sodium bicarbonate to ca. pH 6 and concentrated in vacuo to ca. 45 g. The solid (sodium chloride) was filtered off and discarded. The filtrate was acidified with 30 ml. of 3N hydrochloric acid to pH 1 to precipitate a dark oil. Ethyl acetate and a seed crystal were added and the mixture kept overnight in the refrigerator. The solid was collected, washed with water and ethyl acetate to give 10.3 g. (88%) of crude product, m.p. 205-210° (dec.) sinters at 120°.

An Analytical sample prepared by recrystallization from water had m.p. 195-200° (dec.) sinters at 95°.

Anal. Calcd. for $C_{10}H_{16}N_2O_4S$: C, 46.14; H, 6.20; N, 10.76 Found: C, 46.37; H, 6.45; N, 10.54.

EXAMPLE 6

Preparation of hexahydro-6a-hydroxy-2-oxo-1H-thieno[3,4-a]imidazole-4-pentanoic acid, methyl ester (methyl ester of hydroxybiotin)

A mixture of 5.38 g. (83%, equivalent to 4.46 g., 15.8 mmol) of the compound of Example 2 or 3,200 ml. of methanol, 3 ml. of concentrated hydrochloric acid and 2 g. of 10% Pd/C was shaken on a Parr hydrogenator under 50 lbs. of hydrogen for 22 hours. The catalyst was filtered off. The filtrate was cooled in an ice bath and treated with a solution of 3.2 g. (40 mmol) of potassium cyanate in 20 ml. of water. This mixture was allowed to stand at room temperature for 1 hour, filtered and concentrated in vacuo. The residue was partitioned between 100 ml. of methylene chloride and 50 ml. of water (emulsion). The organic phase was dried over sodium sulfate and concentrated in acuo to leave 4 g. of red oil. This was dissolved in methylene chloride and filtered through 40 ml. of silica. The silica was eluted with methylene chloride, ethyl acetate and tetrahydrofuran. The residue from the tetrahydrofuran eluate was recrystallized from 10 ml. of ethyl acetate to give 0.8 g. of product, m.p. 111-114°.

An analytical sample prepared by recrystallization from water had m.p. 116-120°; IR and nmr ( which indicated a 1:1 mixture of stereo isomers) were used to confirm the structure.

Anal. Calcd. for $C_{11}H_{18}N_2O_4S$: C, 48.16; H, 6.61; N, 10.21. Found: C, 51.72; H, 6.25; N, 10.96.

EXAMPLE 7

Preparation of d,1-2,3,4,6-tetrahydro-2-oxo-1H-thieno[3,4-d]imidazole-4-pentanoic acid (dehydrobiotin)

A mixture of 5.3 g. (20 mmole) of the compound of Example 4, 25 ml. of acetic acid and 2 ml. of acetic anhydride was warmed at 40-50° for 1.5 hours and then filtered to remove a small amount of solid. The filtrate was diluted with 25 ml. of water and cooled in an ice bath. The solid was collected, washed with 50% aqueous acetic acid and then with ether and dried to give 3.24 g. (65%) of product, m.p. 205-210° (dec.).

An analytical sample prepared by recrystallization from water with charcoal had m.p. 210-214° (dec.). IR, UV and nmr confirmed the structure.

Anal. Calcd. for $C_{10}H_{14}N_2O_3S$: C, 49.57; H, 5.82; N, 11.56. Found: C, 49.61; H, 5.18; N, 11.48.

As stated hereinbefore, the product assumed to be dehydrobiotin by Safir et al. had a melting point of 175-176° C. as compared to the product obtained by this procedure.

EXAMPLE 8

Preparation of d,1-2,3,4,6-tetrahydro-2-oxo-1H-thieno[3,4-d]imidazole-4-pentanoic acid, methyl ester (dehydrobiotin methyl ester)

To a suspension of 4.41 g. (64% pure; equivalent to 2.83 g. [10 mmol]pure) of the compound of Example 2 or 3 in 50 ml. of methanol cooled to 10° in an ice bath was added 11 ml. of concentrated hydrochloric acid during 5 minutes. Then 5 g. of zinc dust was added in portions during 5 minutes till the stirred mixture temperature rose to 30°. The reaction mixture was then heated to 60° for 15 minutes. The excess zinc was filtered off and washed with a little methanol. The filtrate was cooled to 10° and mixed with a solution of 2.4 g. (30 mmol) of potassium cyanate in 10 ml. of water. This mixture was allowed to stand at room temperature for 45 minutes, concentrated in vacuo to 25 g,. diluted with 25 ml. of water and extracted with 2×50 ml. of ethyl acetate. The organic extracts were combined, washed with brine, dried over sodium sulfate and concentrated in vacuo to leave 4.1 g. of brown oil. This was dissolved in 10 ml. of acetic acid and 1 ml. of acetic anhydride. The solution was allowed to stand overnight and then concentrated in vacuo. The residue was dissolved in methylene chloride and chromatographed over 50 g. of silica. The column was eluted with methylene chloride, ethyl acetate and tetrahydrofuran. Tetrahydrofuran eluted 1.6 g. of red-brown tar which was extracted with 35 ml. of boiling water. On cooling, the aqueous solution deposited the product, m.p. 168–171°.

Recrystallization from water gave an analytical sample, m.p. 169–173° (dec.): IR, UV, and nmr confirmed the structure.

Anal. Calcd. for $C_{11}H_{16}N_2O_3S$: C, 51.54; H, 6.29; N, 10.93.

Found: C, 51.72; H, 6.25; N, 10.86.

As stated in the Safir et al. article, the product assumed to be the methyl ester of dehydrobiotin, had a melting point of 123–124° C. as compared to the product obtained herein.

The following examples illustrate the formation of biotin by the reduction of dehydrobiotin.

EXAMPLE 9

According to this example dehydrobiotin is reduced to biotin using sodium borohydride as the reducing agent.

To a suspension of 0.48 g. (2 mmole) of d,1-2,3,4,6-tetrahydro-2-oxo-1H-thieno[3,4-d]imidazole-4-pentanoic acid (d,1-dehydrobiotin) in 10 ml. of water cooled in an ice bath was added 0.5 g. of sodium borohydride in portions during 5 minutes. A little ether was added to control foaming. After 15 minutes the ice bath was removed and the reaction mixture was stirred at ambient temperature for 2 days. It was then acidified with acetic acid and concentrated in vacuo. The residue was dissolved in ca. 40 ml. of methanol and reconcentrated in vacuo. This methanol treatment was repeated twice more to leave 1.9 g. of solid. This was suspended in 2 ml. of water. The suspension was acidified with 1 ml. of acetic acid, 2 ml. of 3N hydrochloric acid and concetrated hydrochloric acid to pH 2. This mixture was heated to boiling and allowed to cool to give crude d,1-biotin, m.p. 175–215°. Recrystallization from water gave pure d,1-biotin, m.p. 232–234°.

The nmr spectrum and vapor phase chromatography (VPC) of the crude indicates that it is 65–75% d,1-biotin.

EXAMPLE 10

This example utilizes borane-trimethylamine complex as the reducing agent.

A mixture of 0.24 g. (1 mmole) of d,1-dehydrobiotin, 0.29 g. (4 mmoles) of borane-trimethylamine complex, 2 ml. of dioxane, 1 ml. of water and 0.2 ml. of 10.5N hydrochloric acid was heated under reflux for 2 hours. Thin layer chromatography (2% HOAc, 10% ethanol in ethyl acetate on silica gel G) indicated no starting material left. The reaction mixture was then diluted with 2 ml. of 6N hydrochloric acid and heated under reflux overnight. It was then concentrated in vacuo, the residue was dissolved in methanol and reconcentrated in vacuo. The methanol treatment was repeated twice more. The residue was dissolved in 8 ml. of boiling water. The solution was filtered, concentrated to 4 ml. and cooled to give crude d,1-biotin, m.p. 195–200° C (dec.). The nmr spectrum indicates approximately 50% purity.) Recrystallization from water gave d,1-biotin, m.p. 232–234°.

EXAMPLE 11

The reducing agent used in this example is borane-trimethylamine complex in acetic acid.

A mixture of 0.48 g. (2 mmol) of d,1-dehydrobiotin, 3 ml. of acetic acid, and 0.3 g. of borane-trimethylamine complex was heated on the steam bath for 21 hours. It was then diluted with 5 ml. of 3N hydrochloric acid and heating continued for 2 hours. It was then concentrated in vacuo. The residue was dissolved in water and reconcentrated. This residue was dissolved in methanol and reconcentrated three times to leave 1 g. of residue. This was recrystallized from 20 ml. of water to give crude d,1-biotin, m.p. 165–203°. (VPC indicates 50%) Further recrystallization from water gave d,1-biotin, m.p. 232–234°.

EXAMPLE 12

The reducing agent employed in this example is the triethylsilane/trifluoroacetic acid system.

To a solution of 0.48 g. of dehydrobiotin methyl ester dissolved in 4 ml. of trifluoroacetic acid is added 1 ml. of triethylsilane. The mixture, is allowed to stand at ambient temperature with occasional shaking for two hours. Excess reagents are evaporated under water pump vacuum. The residue is dissolved in 20 ml. of methylene chloride and the solution washed with 10 ml. of saturated sodium bicarbonate solution. The aqueous phase is washed with 10 ml. of methylene chloride. The combined organic phases are dried over sodium sulfate and concentrated in vacuo to leave 0.6 g. of oil. This residue is crystallized with water and hexane to give crude d,1-biotin methyl ester, m.p. 90–105°. Nmr analysis indicates a 65% content of d,1-biotin methyl ester. Recrystallization from methanol or ethyl acetate gives pure d,1-biotin methyl ester, m.p. 130–132°.

EXAMPLE 13

This Example illustrates the preparation of the compound of Example 2 employing as a starting material 7-nitro-6-heptenoic acid, methyl ester.

To a mixture of 3.74 g (20 mmole) of 7-nitro-6-heptenoic acid, methyl ester, 2 g (22 mmole) of mercaptoacetic acid and 10 ml. of ether was added 5 drops of triethylamine. The reaction mixture was allowed to stand for 17 hr. at which time thin-layer chromatography (10% MeOH/CHCl$_3$ or 25% EtOAc/hexane on silica gel G plates) indicated only a trace of starting material. To form the acid chloride 1.84 ml. (25 mmole) of thionyl chloride and b 5 drops of dimethylformamide were added. The reaction mixture was reflux for 1.5 hr. Then 4.94 g. (25 mmole) of 2,4,5-trichlorophenol was added to the reaction mixture and it was heated under reflux for 1 hr. more. It was then cooled in an ice bath and treated with 0.5 ml. of thionyl chloride. It was then treated with a total of 10.4 ml. (75 mmole) of triethylamine in four portions at ca. 0.5 hr. intervals. After a total of 3 hr. of stirring the reaction mixture was diluted with 25 ml. of ether and 45 ml. of saturated brine. After 15 min. of stirring the product was collected and washed with brine, ether and methanol. Recrystallization from methanol gave a pure product, m.p. 193–196° (dec.).

Distillation of 6-acetoxy-7-nitro-heptenoic acid methyl ester at 0.1-0.5 mm gave 7-nitro-6-heptenoic acid methyl ester, b.p. 115°/0.25 mm - 125°/0.4 mm.

EXAMPLE 14

Resolution of 6-carboxymethylthio-7-nitroheptanoic acid, methyl ester

A mixture of 86.7 g. (0.188 mole) of 6-carboxymethylthio-7-nitroheptanoic acid, methyl ester, dicyclohexylamine salt, 400 ml. of water, 900 ml. of ether and 95 ml. of dilute sulfuric acid ($\frac{1}{4}$, v/v) was shaken until the solid dissolved. The organic phase was separated, washed with water and treated with 24.5 ml. (23.2 g., 0.192 mole) of (+)-1-phenylethylamine. This mixture was stirred for 10 minutes and then cooled in a dry ice/acetone bath. The ether was decanted from the oily semisolid which was crystallized from ethyl acetate/ether to 0° to give 26.6 g. (0.0665 mol, 70%) of crude (+)-salt: m.p. 85°–91°; $[\alpha]_D^{25}$ + 5.47° (c 1, CHCl$_3$). The mother liquor was concentrated in vacuo to 38.3 g. of oil which was shaken with 190 ml. of water, 350 ml. of ether and 85 ml. of dilute sulfuric acid ($\frac{1}{4}$). The organic phase was separated, washed with water, treated with 12 ml. (11.4 g., 0.094 mole) of (−)-1-phenylethylamine and cooled in a dry ice/acetone bath. The ether was decanted from the precipitated oil, which was crystallized from ethyl acetate/ether to give 10.2 g. (25.5 mmole, 27%) of (−)-salt m.p. 97°-98.5°; $[\alpha]$ − 8.49° (c 1, CHCl$_3$: Recrystallization from ethanol/ether save a sample for analysis: m.p. 97°-99°; $[\alpha]_D$ − 7.08 (c 1, CHCl$_3$).

Anal. Calcd for C$_{18}$H$_{28}$N$_2$O$_6$S: C, 53.98; H, 7.05; N, 6.99. Found: C, 54.15; H, 7.09; n, 6.79.

EXAMPLE 15

Resolution of 5-(4-oxo-3-nitrotetrahydrothien-2-yl)pentanoic acid, methyl ester

A mixture of 33.73 g. (containing 14.16 g., 50 mmole) of crude (42% pure by uv) 5-(2,5-dihydro-4-hydroxy-3-nitrothien-2yl) pentanoic acid, methyl ester sodium salt, 100 ml. of ether, 50 ml. of water and 10 ml. of dilute sulfuric acid ($\frac{1}{4}$, v/v) was shaken until most of the solid was in solution. The ethereal phase was separated and washed with 50 ml. of water acidified with 2 ml. of dilute sulfuric acid. The aqueous phases were washed in turn with 50 ml. of ether; the two ethereal extracts were combined and dried over sodium sulfate. A little tar was removed by filtration through Celite. The filtrate was treated with 3.2 ml. (25 mmole) of (−)-1-phenylethylamine. Crystallization was induced by scratching and the mixture was stirred in an ice-bath. The solid was collected, washed with ether, and dried to give 9 g. (94%) of the levo-rotatory salt, m.p. 125°-130° (dec); $[\alpha]_D^{25}$ − 190° (c 1, CHCl$_3$). An analytical sample prepared by recrystallization from methanol had m.p. 137°-138°; $[\alpha]25/D$ − 220° (c 1, CHCl$_3$).

Anal. Calcd for C$_{18}$H$_{26}$N$_2$O$_5$S: C, 56.53; H, 6.85; N, 7.32. Found: C, 56.21, H, 6.95, N, 7.22.

The above ethereal mother liquor was washed with 50 ml. of water acidified with 2 ml. of dilute sulfuric acid and dried over sodium sulfate. To this solution of nitro ketone was added 3.2 ml. (25 mmole) of (+)-1-phenyl-ethylamine. After this mixture had been stirred in an ice bath, the crude dextrorotary isomer was collected, washed with ether and dried to give 9.34 g. (98%); m.p. 125°-130° (dec); $[\alpha]_D^{25}$ + 260° (c 1, CHCl$_3$). An analytical sample prepared by recrystallization from methanol had m.p. 127°-9° (dec); $[\alpha]_D^{25}$ + 215° (c 1, CHCl$_3$).

Anal. Calcd. for C$_{10}$H$_{15}$NO$_5$S.C$_8$H$_{11}$N: C, 56.53; H, 6.85; N, 7.32. Found: C, 56.75; H, 6.90; N, 7.38.

EXAMPLE 16

(−)-5-(2,5-dihydro-4-hydroxy-3-nitrothieno-2-yl)pentanoic acid, methyl ester, dicyclohexylamine salt A mixture of 19.6 g. (49 mmole) of (+)-6-carboxymethylthio-7-nitroheptanoic acid, methyl ester, (+)-α-methyl benzylamine salt, 200 ml. of ether, 100 ml. of water and 20 ml. of dilute sulfuric acid ($\frac{1}{4}$, v/v) was shaken until the solid had dissolved. The organic phase was separated, washed with 50 ml. of water and 50 ml. of brine and dried over calcium sulfate. To the filtered ether solution was added 10.6 g. of 2,4,5-trichlorophenol, and it was cooled in an ice bath to 5°. Then a solution of 11.5 g. of N,N'-dicyclohexylcarbodiimide in 20 ml. of ether was added. This reaction mixture was stirred in the ice bath for 30 minutes and then at room temperature for 40 minutes. The precipitated dicyclohexyl urea was filtered off and washed with ether. The filtrates were cooled to 5° in an ice bath and treated with 8 ml. of triethylamine and then stored in the refrigerator for 4 days. To the stirred reaction mixture was added 150 ml. of saturated sodium chloride solution. The precipitate was collected, washed with a small amount of cold water and ether and dried briefly to give 53 g. of solid which by uv analysis contained 9.4 g. (68%) of the sodium salt of the product.

This solid was shaken with 100 ml. of ether, 50 ml. of water and 5 ml. of dilute sulfuric acid ($\frac{1}{4}$, v/v) until the solid dissolved. The organic phase was separated, washed with 50 ml. of water, dried over calcium sulfate, filtered and treated with 9 ml. of dicyclohexylamine. After the mixture had been cooled in the refrigerator over night, the solid was collected, washed with ether and dried to give 11.4 g. (52%) of product; 126°-130°; $[\alpha]_D$ −234° (c 1, CHCl$_3$). Recrystallization from acetonitrile gave an analytical sample; m.p. 128°-130°; $[\alpha]_D$ −234° (c 1, CHCl$_3$).

Anal. Calcd for C$_{10}$H$_{15}$NO$_5$S.C$_{12}$H$_{23}$N: C, 59.70; H, 8.65; N, 6.33. Found: C, 59.66; H, 8.78; N, 6.40.

EXAMPLE 17

(−)-2,3,4,6-Tetrahydro-2-oxo-1H-thieno[3,4-d]imidazole-4-pentanoic acid (1-dehydrobiotin)

A mixture of 2.8 g. (6.3 mmole) of (−)-5-(2,5-dihydro-4-hydroxy-3-nitrothieno-2-yl)pentanoic acid, methyl ester, dicyclohexylamine salt, 100 ml. of acetic acid, 15 ml. of 3N hydrochloric acid and 0.7 g. of 10% Pd/C was shaken under 50 lbs. of hydrogen for 21 hours. The reaction mixture was filtered through Celite which was washed with water. The filtrates were concentrated in vacuo at a bath temperature of 40° to semisolid. This was diluted with water and reconcentrated to 7.4 g. of residue. This was diluted with 25 ml. of water. The preciptiate was filtered off; the filtrate was washed with 25 ml. of ether, treated with a solution of 1.5 g. of potassium cyanate in 10 mol of water and stirred for 1 hour at room temperature. It was then diluted with 10 ml. of 2N sodium hydroxide (pH 12) and let stand at room temperature for 1.5 hour. The pH was then adjusted to 7 with 3N hydrochloric acid, and it was concentrated in vacuo at 40° to 8.3 g. This was diluted with 5 ml. of water made strongly acidic with 3N hydrochloric acid and cooled. The solid was collected, washed with a small amount of water and dried to give 1.1 g. This was dissolved in 15 ml. of acetic acid and 10 drops of trifluoroacetic acid, warmed to 50° allowed to stand for 30 minutes and concentrated in vacuo at 40°. This dissolution in acetic acid was repeated twice more and then the residue was diluted with 10 ml. of ethyl acetate. The solid was collected and recrystallized from methanol to give 0.23 g. of product, m.p. 189°–199°; $[\alpha]_D^{20}$ — (c 1, 0.1N NaOH).

Anal. Calcd. for $C_{10}H_{14}N_2O_3S$: C, 49.57; H, 5.82; N, 11.56. Found: C, 49.38; H, 5.94, N, 11.61.

EXAMPLE 18 d-Biotin

To a solution of 0.48 g. (2 mmole) of (—)-dehydrobiotin (—)-2,3,4,6-tetrahydro-2-oxo-1H-thieno[3,4-d]imidazole-4-pentanoic acid in 5 ml. of trifluoroacetic acid was added 1 ml. of triethylsilane and the mixture was allowed to stand at room temperature overnight. The reaction mixture was concentrated in vacuo to a mixture of brown tar and a colorless liquid which was decanted off. The tar was crystallized three times from water (once with charcoal) to give 0.10 g. of d-biotin, m.p. 228°–230°; $[\alpha]_D^{25}$ + 90.2° (c 0.57, 0.1N NaOH).

EXAMPLE 19

(+)-5-(2,5-Dihydro-4-hydroxy-3-nitrothien-2-yl)pentantoic acid, methyl ester, dicyclohexylamine salt A mixture of 9.8 g. (24.5 mmole) of 6-carboxymethylthio-7-nitroheptanoic acid methyl ester, (—)-α-methylbenylamine salt ($[\alpha]_D$ = 5.46°) and 100 ml. of ether was shaken with 50 ml. of water plus 10 ml. of dilute sulfuric acid (¼, v/v). The organic phases was separate, washed with 25 ml. of water and 25 ml. of brine and dried over sodium sulfate. To this solution after the drying agent has been filtered off was added 5.33 g. (27 mmole) of 2,4,5-trichlorophenol. To this solution stirred in an ice bath at 0°–5° was added 5.77 g. (28 mmoles) of N,N'-dicyclohexylcarbodiimide in 10 ml. of anhydrous ether. After this mixture has stirred 0.5 hours, the ice bath was replaced with water bath at 25° and stirring was continued for a further 45 minutes. The precipitated dicyclohexylurea was filtered off and washed with ether. The filtrate was cooled to 0°–5° and treated with 4 ml. (29 mmol) of triethylamine. This mixture was allowed to stand for 3 days at 0° and then diluted with 60 ml. of saturated brine, to give an immediate voluminous precipitate. This was collected, washed with a few ml. of water and then ether, and dried in vacuo to give 7.2 g. of crude material, containing 3.42 g. (by uv, 49% yield) of sodium salt. This was converted to the dicyclohexylamine salt for characterization. The solid was shaken with 50 ml. of ether and 25 ml. of water and the aqueous phase was made strongly acidic by the addition of ca 2 ml. of dilute sulfuric acid (¼, v/v). The organic phase was separated, washed with 25 ml. of water and dried over sodium sulfate. To the filtered solution was added 3 ml. (15 mmole) of dicyclohexylamine. After standing overnight at 0° the product was collected and washed with ether to give 5 g. (46%) of product, m.p. 124°–8° (dec). $[\alpha]_D^{25}$ + 203.8 (c 1, CHCl₃).

Anal. Calcd for $C_{22}H_{38}N_2O_5S$: C, 59.70; H, 8.65; N, 6.33. Found: C, 59.76; H, 8.51; N, 6.33.

EXAMPLE 20 l-Biotin

To a solution of 0.48 g. (2 mmole) of (+)-dehydrobiotin ($[\alpha]_D^{25}$ + 41°) in 5 ml. of trifluoroacetic acid was added 1 ml. of triethylsilane and the mixture allowed to stand at room temperature for 4 days. The reaction mixture was concentrated in vacuo to a mixture of a brown tar and a colorless liquid. The liquid was decanted off and the residue crystallized from ca. 2 ml. of water to give 0.43 g. (wet weight) of crude product, m.p. 175–190°. Two recrystallizations from water, one with addition of charcoal, gave 0.11 g. of 1-biotin; m.p. 224°–226°; $[\alpha]_D$ — 87.5° (c 1, 0.1N NaOH). Further identified by its nmr spectrum.

EXAMPLE 21 d-2,3,4,6-tetrahydro-2-oxo-1H-thieno[3,4-d]imidazole-4-pentanoic acid (d-dehydrobiotin)

A mixture of 2.8 g. (6.33 mmole) of nitroketone dicyclohexylamine salt (dicyclohexylamine salt of compound (VIIIa), 100 ml. of glacial acetic acid, 10 ml. of 3N hydrochloric acid and 0.7 g. of 10% Pd/C was hydrogenated at 50 psi on a Parr shaker for 16 hours. This mixture was filtered through Celite to remove catalyst and the filtrate concentrated in vacuo at 40°. The residue was diluted with water and reconcentrated to 8.7 g. To this was added 25 ml. of water and the precipitate filtered off. The filtrate was washed with 25 ml. of ether, treated with 1.5 g. (18.5 mmole) of potassium cyanate and allowed to stand at room temperature for 1 hour. The pH of the solution was approximately 4. Thin layer chromatography indicated a ca 1:1 mixture of hydroxybiotin and its methyl ester. The pH of the solution was adjusted to 7 by the addition of 12 ml. of 1N sodium hydroxide. Then an additional 1N sodium hydroxide was added and the mixture warmed to 50°. After 0.5 hour, the pH had fallen to 8 and tlc indicated ester still present. A further 5 ml. of 3N sodium hydroxide was added and the reaction allowed to stand for 1 hour at room temperature at which time tlc indicated only a trace of ester left. The pH was adjusted to 7 with 3N hydrochloride acid, and the reaction mixture filtered to remove a little tar. The filtrate was concentrated in vacuo to 5.2 g., diluted with 5 ml. of water and made strongly acidic with 3N hydrochloric acid. The precipitate was collected and washed with a little water to give hydroxybiotin (wet weight 2 g.). This was dissolved in 15 ml. of acetic acid plus 10 drops of trifuloroacetic acid by warming to 50°. After 0.5 hour tlc indicated the presence of hydroxybiotin. The reaction mixture was concentrated in vacuo (water bath at 40°) to 2.8 g. and redissolved in 15 ml. of acetic acid plus 10 drops of trifluoroacetic acid. After a total of three dissolutions tlc indicated little hydroxybiotin left. The mixture was filtered, concentrated in vacuo to 1.6 g. and diluted with 10 ml. of ethyl acetate to precipitate 1 g. (65%) of (+)-dehydrobiotin; m.p. 180°–185° (d); $[\alpha]_D$ +

41.0° (c 1, 0.1 N NaOH). Recrystallization from water gave prisms; m.p. 187°-197° (d); (1832, 5331-92).
I claim:
1. A compound of the formula:
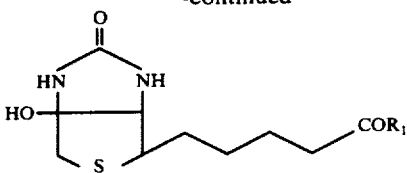
IX
wherein $R_1$ is lower alkoxy, hydroxy, lower alkyl substituted or unsubstituted amino;
the racemates and optical antipodes thereof.
2. The compound of claim 1 wherein $R_1$ is hydroxy.
3. The compound of claim 1 wherein $R_1$ is methoxy.
* * * * *